(12) United States Patent
Shin

(10) Patent No.: US 7,264,598 B2
(45) Date of Patent: Sep. 4, 2007

(54) FAR INFRA-RED RAY AND ANION EMITTING THERMAL ROTARY MASSAGER FOR DECREASING FATS IN THE ABDOMINAL REGION OF A HUMAN BODY EQUIPPED WITH ROTATING ELECTRIC CONNECTORS

(76) Inventor: Thomas J B Shin, 4030 W. 7th St., Los Angeles, CA (US) 90005

( * ) Notice: Subject to any disclaimer, the term of this patent is extended or adjusted under 35 U.S.C. 154(b) by 0 days.

(21) Appl. No.: 11/724,671

(22) Filed: Mar. 16, 2007

(65) Prior Publication Data

US 2007/0173748 A1    Jul. 26, 2007

Related U.S. Application Data

(63) Continuation-in-part of application No. 11/008,624, filed on Dec. 10, 2004, now abandoned.

(51) Int. Cl.
*A61H 15/02* (2006.01)
*A61H 7/00* (2006.01)

(52) U.S. Cl. .................. 601/15; 601/87; 601/112; 601/113

(58) Field of Classification Search ............. 601/15, 601/16, 18, 22, 27, 28, 31–32, 46, 49, 50, 601/69, 70, 84, 85, 87, 102–104, 112, 113, 601/128, 131, 136; 607/99, 102
See application file for complete search history.

(56) References Cited

U.S. PATENT DOCUMENTS

| | | | | |
|---|---|---|---|---|
| 5,336,159 A | * | 8/1994 | Cheng | 601/15 |
| 5,486,156 A | * | 1/1996 | Takach | 601/70 |
| 6,149,611 A | * | 11/2000 | Chen | 601/22 |
| 6,454,732 B1 | * | 9/2002 | Lee | 601/101 |
| 6,511,446 B1 | * | 1/2003 | Wu | 601/15 |
| 2003/0009117 A1 | * | 1/2003 | Zou | 601/134 |
| 2005/0209538 A1 | * | 9/2005 | Lev et al. | 601/15 |

\* cited by examiner

*Primary Examiner*—Quang D. Thanh

(57) ABSTRACT

A thermal rotary massager is provided. The thermal rotary massager according to current application is comprised of two noble rotary electric connectors to heat four heaters embedded inside of four massage balls while the massage balls are rotating. Each electric connector according to current application is comprised of a seating member and one metal bearing connection parts for conduction of electricity. The seating member fits on ribs that is formed on the upper surface of a case and does not rotate. However, the massage balls are heated to emit far-infrared ray and anions while they are rotate-ably massaging user's body. It is possible due to the rotary connectors.

2 Claims, 5 Drawing Sheets

FAR INFRA-RED RAY AND ANION EMITTING THERMAL ROTARY MASSAGER FOR DECREASING FATS IN THE ABDOMINAL REGION OF A HUMAN BODY EQUIPPED WITH ROTATING ELECTRIC CONNECTORS

Current application is a continuous in part of previous application Ser. No. 11/008,624 filed Dec. 10, 2004, which is now abandoned.

FIELD OF THE INVENTION

The present invention relates to a massager, especially to a massager which is equipped with special rotary electric connectors for heating massage balls while rotate-ably massaging the human body and emitting far-infrared ray and anions.

BACKGROUND OF THE INVENTION

Most of rotary massage apparatus of prior art do not have heating elements that emits far infra-red ray or anions, which are known as effective for chronic diseases, such as constipation or digestive disorder. It was impossible because electrical connections for such rotating massage balls are not developed. Moreover, the relative position of the massage balls are designed without a significant consideration of the special nerve parts on the abdominal portion of a human body that are known to essential part for curing/preventing chronic diseases, such as constipation or digestive disorder. As a result, the rotary massager of the prior art are not effective for facilitating the circulation of blood, relaxing muscles, and reducing fats in the abdominal region of a human body. It is purpose of the current application to provide a rotating electricity connector for a massaging apparatus that emits anions and far infrared ray while rotatably massaging human body.

DESCRIPTION OF PRIOR ARTS

U.S. Patent Application 20050209538 to Lev, Mordechai; et al. illustrates a massage apparatus which includes a housing, a motor disposed within the housing, and at least one massage center provided on the housing. The massage center includes an outer massage member and an inner massage member, where the outer massage member at least partially circumferentially surrounds the inner massage member. The outer and inner massage members are operably connected to the motor for providing rotation of the massage members.

United States Patent Application 20030009117 to Zou, Jian-Han illustrates a kneading head of massage machine that consists of a connecting rod and a set of spherical heads. One set of the spherical heads includes two and more; all the spherical heads located on ends of the connecting rod in different heights, or all the spherical heads can be integrated with the connecting rod into a whole body. When the massage machine adapting the kneading head is used on the human body, the stepped spherical heads will effort a great pushing force and a great pressing force on surface and deeper skin of the muscle of the human body simultaneously at different heights and positions so as to carry on massage in kneading method with a better effect for meeting the necessaries of the customers.

U.S. Pat. No. 6,454,732 to Lee illustrates an apparatus for rising and falling a medicator of an automatic hot-heat treatment device, includes: a movement space formed vertical to a main body of a movable body horizontally moving along with a screw rotated by a motor; a treatment device moving plate having a carrying bar insertedly bound with the movement space and moving in the movement space its horizontal movement and a jaw at the lower end portion of the carrying bar; and a rising and falling spring positioned between the treatment device moving plate and the movable body, for moving the madicator up and down so as to be tensed and contracted according to the curve of the body of the user to thereby pressurize and foment the diseased part of the user.

U.S. Pat. No. 5,486,156 to Takach illustrates a vibrating, form fitting skull cap which is designed to snugly fit a user. The inner portion of the cap presents a smooth continuous surface to the head while at the same time providing the capability of complex and subtle vibration patterns which may vibrate different areas differently. Suitable attachment points are provided on the outer portion of the cap to mount individual forced vibration generator units. Each vibration generator unit is separately controlled as to amplitude and frequency. The user may choose one or many of numerous available attachment points for the generators. Electrical controls are provided to fine tune the individual units. Numerous electrical power input alternatives are provided for flexibility of use. Pneumatic powered units may also be used to eliminate magnetic fields if necessary.

U.S. Pat. No. 5,336,159 to Cheng illustrates an infrared massager includes two massaging devices respectively locked in two receiving chambers on a casing by lock hoods, which include each a plurality of silicon rubber massage elements on a vibrating plate reciprocated by a motor through a cam. Two infrared devices are respectively received in the receiving chambers and are attached to the vibrating plate of each massaging device. The infrared devices include a plurality of infrared light emitting elements controlled to emit infrared light through the silicon rubber massage elements for heating the muscles as the muscles are massaged by the massaging devices.

U.S. Pat. No. 5,114,352 to Gahagen illustrates a rotate-able marine electric connector intended to be used in the transmission of electricity from a dock mounted power receptacle to a vessel moored to said dock. The connector comprises an upper rotate-able section to which an electric cable is connected. This upper rotate-able section features a rubber boot which helps seal the inside of the connector from the elements. The upper rotate-able section is operably and electrically connected to a lower rotate-able section. This lower rotate-able section connected electrically with an appropriate connecter to complete the circuit an allow power to be supplied the vessel. The upper rotate-able section may be allowed to rotate freely with respect to the lower rotate-able section, or alternately, a screw may be tightened thereby immobilizing the upper rotate-able section with respect to the lower rotate-able section. However, this rotating electric connector can not rotates 360 degrees to connect electricity in any position as a winder due to its structure.

As a conclusion, none of the prior art illustrates a rotating electricity connector that enables massaging, heating, emitting far-infrared ray and anion at the same the time.

SUMMARY OF THE INVENTION

Most of rotary massage apparatus of prior art do not have heating elements that emits far infra-red ray or anions, which are known as effective for chronic diseases, such as constipation or digestive disorder. It was impossible because electrical connections for such rotating massage balls are not developed. Moreover, the relative position of the massage balls are designed without a significant consideration of the special nerve parts on the abdominal portion of a human body that are known to essential part for curing/preventing chronic diseases, such as constipation or digestive disorder. As a result, the rotary massage apparatus of the prior art are not effective for facilitating the circulation of blood, relaxing muscles, and reducing fats in the abdominal region of a human body. It is purpose of the current application to provide a rotating electricity connector for a massaging apparatus that emits anions and far infrared ray while rotate-ably massaging human body. A thermal rotary massager is comprised of two noble rotary electric connectors to heat four heaters embedded inside of four massage balls while the massage balls are rotating. Each electric connector according to current application is comprised of a seating member and one metal bearing connection parts for conduction of electricity. The seating member fits on ribs that is formed on the upper surface of a case and does not rotate. However, the massage balls are heated to emit far-infrared ray and anions while they are rotate-ably massaging user's body. It is possible due to the rotary connectors.

DETAILED DESCRIPTION OF THE PREFERRED EMBODIMENT

Figure 1:
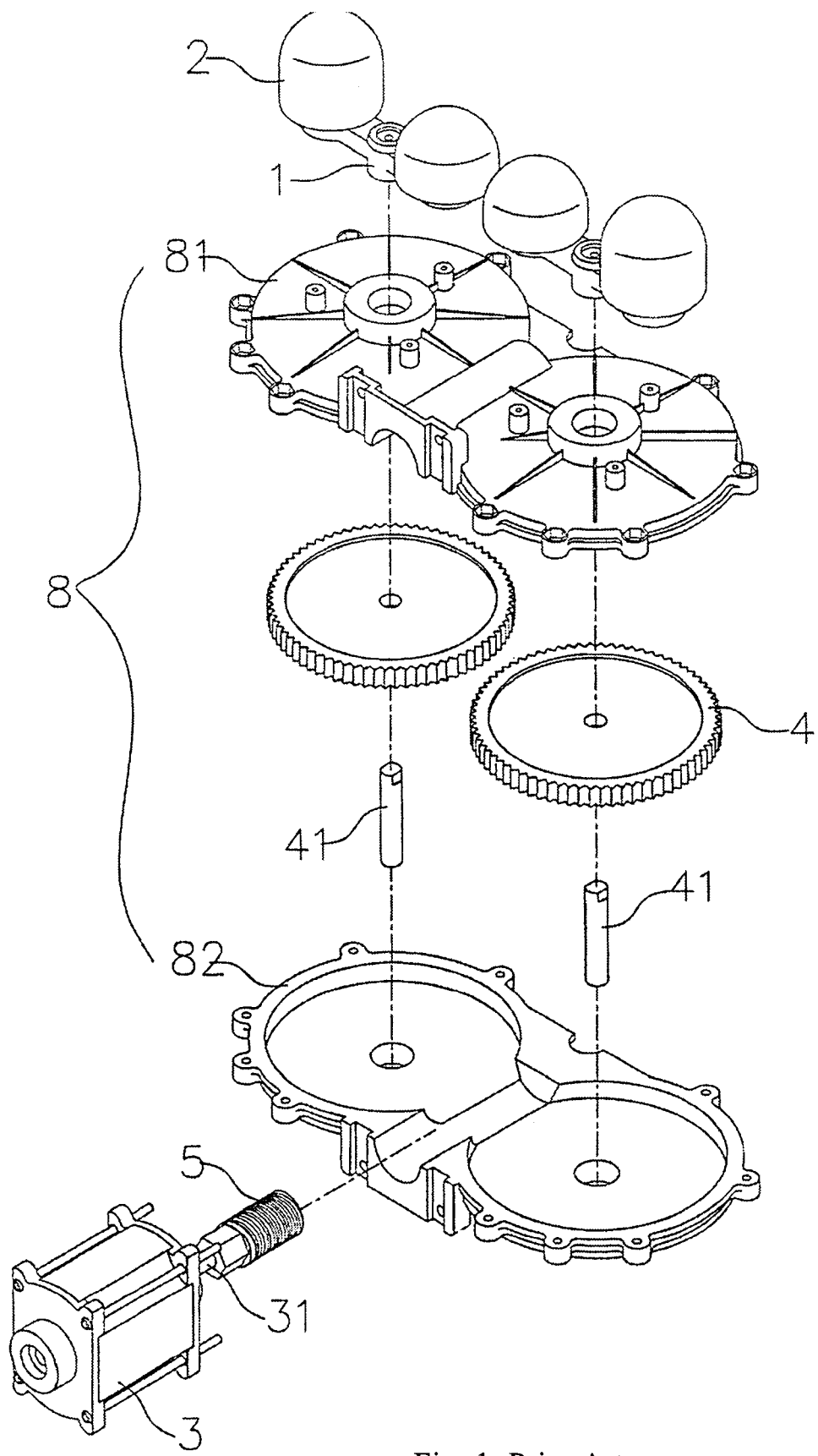
FIG. 1 is an exploded perspective view of a rotary massage apparatus of prior art.
Figure 2:
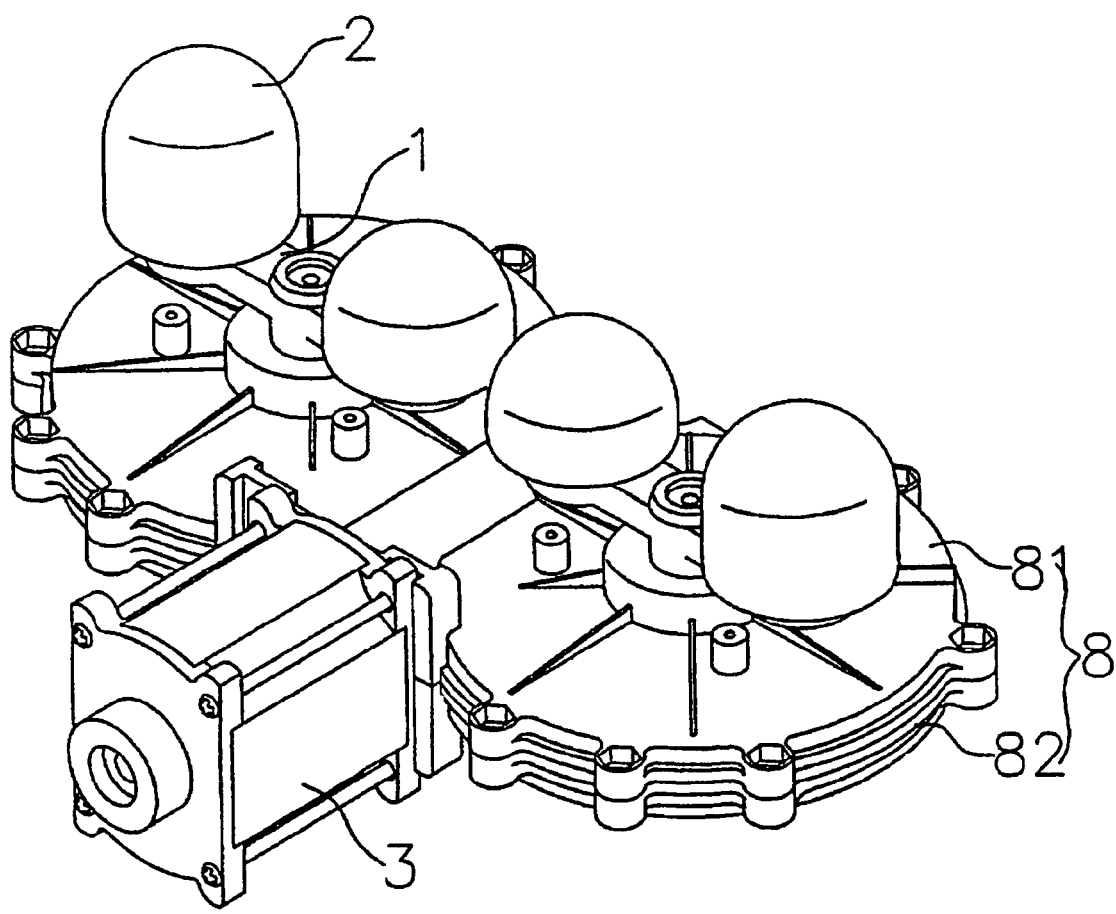
FIG. 2 is a perspective view showing an assembled state of a rotary massage apparatus of prior art.
Figure 3:
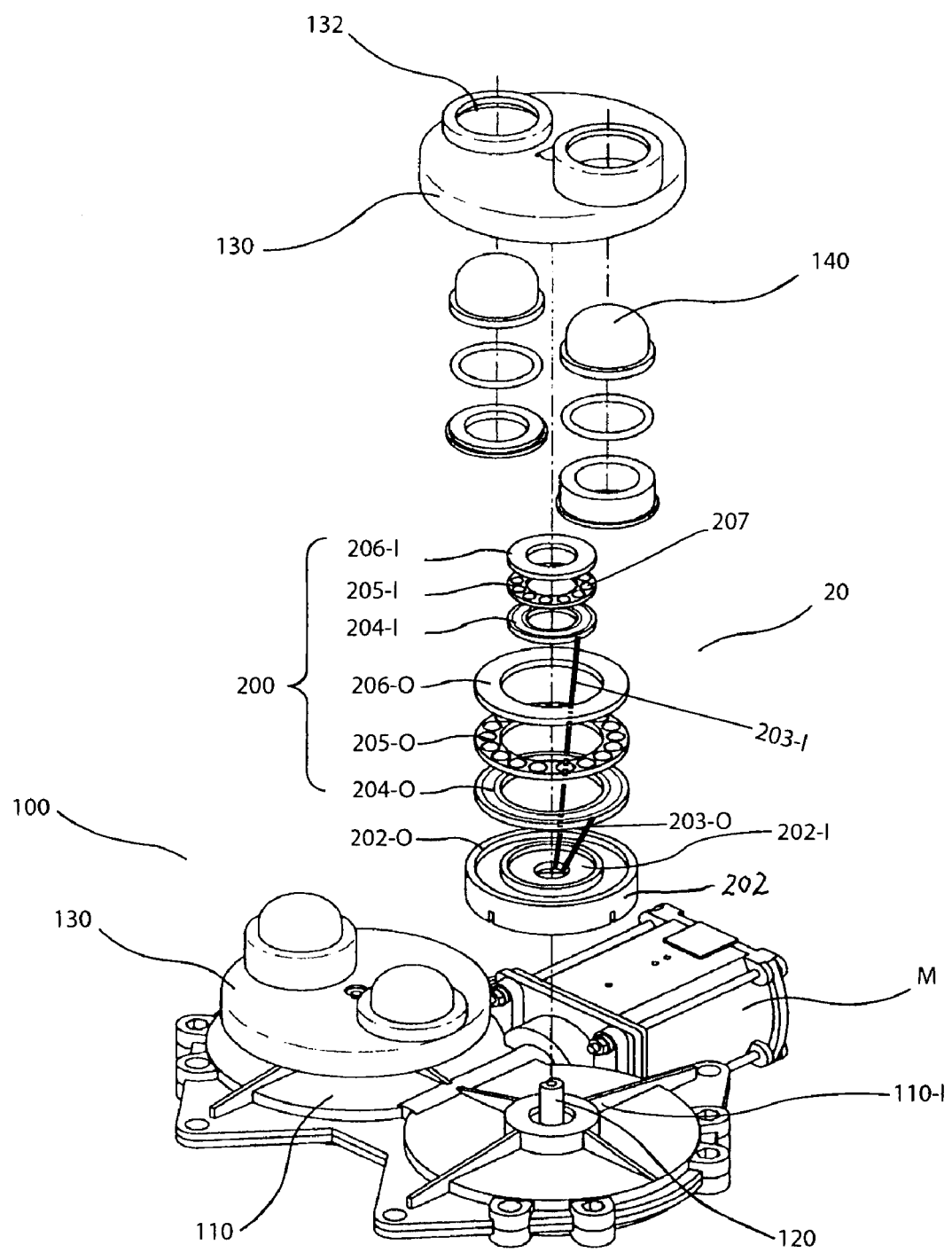
FIG. 3 is an exploded perspective view of a rotary massager according to current application.
Figure 4:
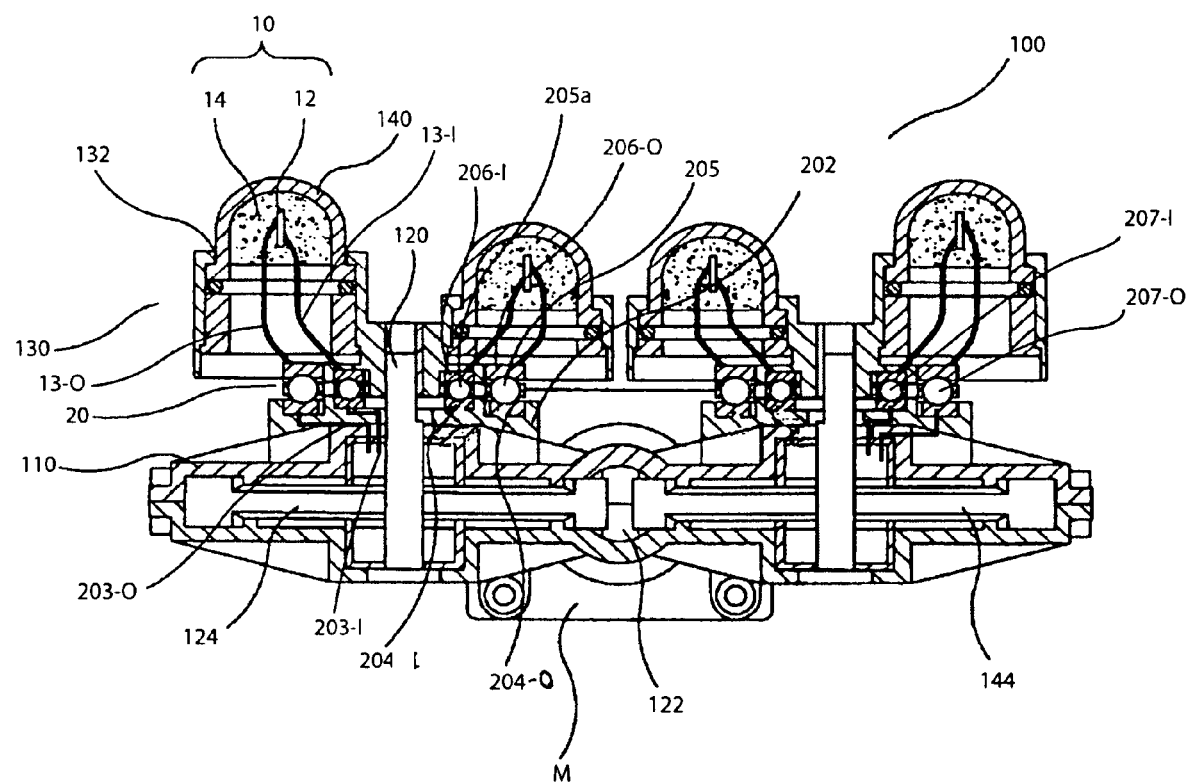
FIG. 4 is a cross-sectional view of a thermal rotary massager according to current application.

FIG. 1 is an exploded perspective view of a rotary massage apparatus of prior art and FIG. 2 is a perspective view showing an assembled state of a rotary massage apparatus of prior art. FIG. 3 is an exploded perspective view of the first embodiment of the rotary massager (100) of the current application. FIG. 4 is a cross-sectional view of a thermal rotary massager according to current application.

As shown in those drawings, base part of the rotary massage apparatus (100) of the current application is same as the prior art. The base part is comprised of a case (110); two rotary shafts (120) rotate-ably connected onto a worm (122) and a pair of worm wheels (124) engaged to the worm (122). The worm (122) and worm wheels (124) are mounted inside a case (110). A motor M rotates the worm (122) in a vertical direction and the worm (122) rotates the worm wheels (124) in a horizontal direction; one rotary shaft (120) is connected to one worm wheel (124) at the center thereof. A rotary plate (130) with two mounting holes (132) is connected to the rotary shaft (120). Two massage balls (140) are engaged to the mounting holes (132) with a predetermined height.

This structure is the same as a prior art of application publication 2003/0009117 by Zou. However, the rotary massage apparatus of Zou's can not supply electricity to the massaging balls 2. Therefore, many improvements are needed to enable the rotary massager of the current application to produce far infrared rays and anions.

The rotary massage apparatus according to the current application further includes four heater (12) and two rotary electric connectors (20).

Each heater (12) is located inside of a massage ball (140) embedded in filling material (14). The heater (12) is made of nickel/chrome wire connected with two electric connecting wires (13-I), (13-O). One end of the inner electric connecting wire (13-I) is welded to the heater (12) and the other end of the inner electric connecting wire (13-I) is welded to an inner upper metal ring (206-I) for supplying electric current. One end of the outer electric connecting wire (13-O) is welded to the heater (12) and the other end of the outer electric connecting wire (13-O) is welded to an outer upper metal ring (206-O) for supplying electric current. Therefore, eight electric connecting wires are needed to connect four heaters (12) to the two rotary electric connectors (20). Each of the heaters (12) is embedded in a filling material (14). Starting filling material is silicon. But, the rubbery silicon is hardened by heating filing material, silicon, above 400° C. and becomes silica that emits far-infrared rays by heating.

Each rotary electric connector (20) includes a seating member (202) and one metal bearing connection part (200) for conduction of electricity. The seating member (202) fits on ribs (110-I) formed on the upper surface of the case (110) and does not rotate. Each metal bearing connection part (200) is comprised of;

1) one outer fixing metal ring (204-O) and one inner fixing metal ring (204-I) that are mounted on an outer groove (202-O) and an inner groove (202-I) of the upper surface of the seating member (202) respectively. Two A/C power lines (203-I) and (203-O) are welded to the inner fixing metal ring (204-I) and the outer fixing metal ring (204-O) respectively from the bottom side and connected to the main power source (not shown in the Figure), 2) one outer upper metal ring (206-O) and one inner upper metal ring (206-I) that are adhered to the bottom surface of the rotary plate (130) and that are connected to outer power supply wire (13-O) and inner power supply line (13-I) for the heater (12) respectively, and 3) one outer rolling ball body (205-O) and one inner rolling ball body (205-I). Each rolling ball body, (205-O) and (205-I), is comprised of plurality of metal rolling balls (207-O) and (207-I) between the fixed metal rings (204-O), (204-I) and the upper metal rings (206-O), (206-I). Size of metal rolling balls in outer rolling ball body (205-O) is larger than the size of metal rolling balls in inner rolling ball body (205-I)

The rotary plate (130), connected with the rotary shaft (120), rotates when the worm (122) and the worm wheels (124) are rotated by driving force of the motor (M), so that the massage balls (140) mounted in the mounting holes of the rotary plate (130) massage the user's body. Meanwhile, the metal rolling balls (207-O), (207-I) in rolling ball bodies (205-O), (205-I) electrically and rotate-ably connect the outer fixing metal ring (204-O) to the outer upper metal ring (206-O) and connect the inner fixing metal ring (204-I) to the inner upper metal ring (206-I).

If the heater (12), which placed inside of the massage balls (140), is directly connected to an electric power source by electric wires, the massage balls (140) will wind up the electric wires because the rotary plate (130), on which the massage balls (140) are placed, rotates with the rotary shaft (120) as electricity is turned on. Then the electric wires (13-I), (13-O) (in this case (13-I) and (13-O) overlaps with (203-I) and (203-O)) will be separated from the heater (12). It is because the distance between the welding point of the heater (12) with electricity wires (13-O), (13-I) and the power source (electricity plug) increases with rotation of the rotary plate (130) while the length of electricity lines (13-O) and (13-I) are fixed. Therefore, Zou's massager, which does not have such rotating connector, can not heat the massage balls and produce far infrared ray and anions.

Meanwhile, Lev renders the massager producing far infrared rays by introducing a printed circuit board that includes far infrared lamps. Lev's heating assembly 83 includes an annular conducting plate 84 disposed in each recess 52 and in electrical communication with switch 30. An annular printed circuit board 86 is mounted between outer massage member base 72 and cover 80, where printed circuit board 86 includes infrared lamps 88 provided thereon. Printed circuit boards 86 are in electrical communication with each conducting plate 84 via a conductor 90, such as a brush, so that electrical communication is maintained while printed circuit board 86 rotates with outer massage member base 72. Upon activation of the massage and heating mode via depression of switch 30, power is supplied to printed circuit board 86 and infrared lamps 88, providing infrared heat to a user's foot via outer massage member 26, not through massage balls 27. Therefore, Lev's massager does not directly heat the massaging balls, which directly contact the user's skin and rotates. Moreover, the infra red lamps 88 are mounted on printed circuit board 86, which is located well below the massage balls 27 and massage members 24, 26. It is well known that the strength of rays decreases along the square of the distance between the light source and the object.

On the other hand, the massage balls according to current application are heated directly and contact directly with the user's body in a heated condition during rotation. Therefore, the massage apparatus of the present invention can more effectively relax muscles of the user's body and promote circulation of blood by massaging certain regions of the user's body in a warm condition. Different from Lev's far infrared lamp, massage balls (140) of current application emits far infrared ray indirectly.

Since the massage balls (140) have different height from the plate (130), the balls can stimulate the special nerve part evenly at the same time such as 'Jung Wan; known as nerve part sensitive to stomach', 'Ha Wan; known as nerve part sensitive to duodenum', 'Shin Kwol (the navel); known as nerve part sensitive to digestive upset', 'Ki Hae; known as nerve part sensitive to kidney', and 'Kwan Won; known as nerve part sensitive to uterus and small intestine', which are positioned at the different depth from the curvature surface of the abdominal portion.

Figure 5:
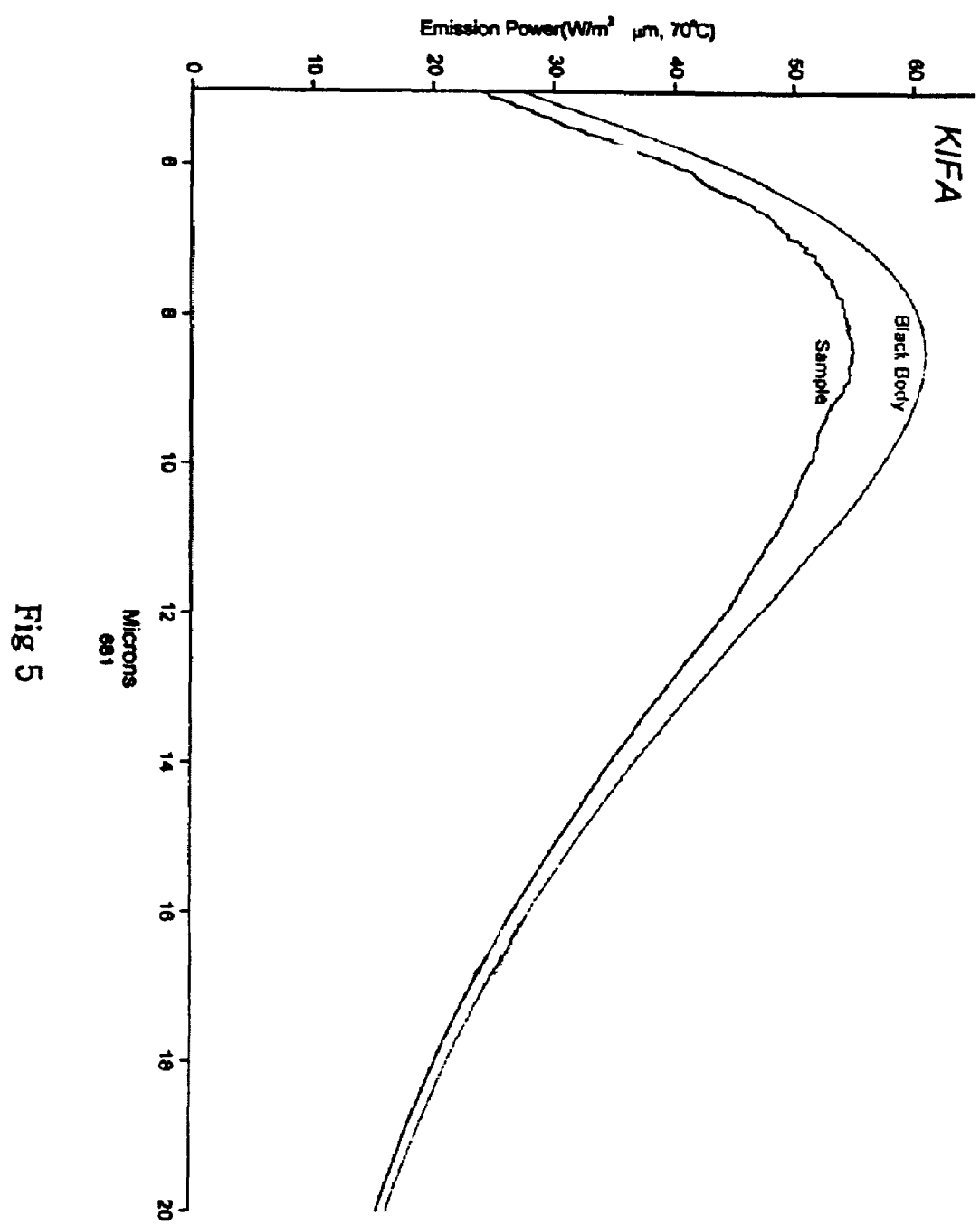
FIG. 5 is a chromatography showing the emission of far infrared ray from the massage apparatus of the current application.

FIG. 5 is a chromatography showing the emission of far infrared ray from the massager of the current application. The curve marked as blue line shows the intensity of light waves at each wave length in micrometer. The curve shows a maximum intensity at the light wave length of shorter than 10 micrometer that is in the far infra-red wave length. That pattern can be observed from the light emitting curve of a black body. Concentration of anions measured by anion particle measuring instrument at the Korea Far Infrared Association is 312 each/cm$^3$.

Table 1. is a reading of fat reducing of a user of the massage apparatus of the current application. After one year use, 15 minutes per one nerve part a day for four nerve parts, the volume of fat in the user's body is measured by the NMR (Nuclear Magnetic Resonance) CT (Computerized Tomography). It shows decrease of 54 cm$^3$ of fat from whole body and among them 18 cm cm$^3$ of fat is decreased from the abdominal portion of the user.

TABLE 1

Readings of Body Fat Change from NMR CT photogram

|  | Total Fat (cm$^3$) | Abdominal Fat (cm$^3$) | Fatness (%) |
| --- | --- | --- | --- |
| Before the Treatment | 325.57 | 74.50 | 22.88 |
| After the Treatment | 271.15 | 56.07 | 20.68 |

Since the massage balls are made of materials for emitting far infrared rays and anion, the massage apparatus of the current application reduces a body fat, especially for abdominal portion's fat, by promoting circulation of blood and metabolism through the massage function.

What is claimed is:

1. A rotary massager with two noble rotary electric connectors to heat four heaters embedded inside of four massage balls while the massage balls are rotating is comprised of;

two seating member which fits on ribs formed on an upper surface of a case and do not rotate, and four electric heaters made of nickel/chrome wire, each of which is located inside of a massage ball and embedded in filling material, and two metal bearing connection parts for conduction of electricity, each of which is comprised of;
one outer fixing metal ring that is mounted on an outer groove of the upper surface of the seating member and welded to an outer A/C electric power line, and
one inner fixing metal ring that is mounted on an inner groove of the upper surface of the seating member and welded to an inner A/C electric power line, and
one outer upper metal ring that is adhered to the bottom surface of a rotary plate and is welded to an outer power supply line of the heater, and
one inner upper metal ring that is adhered to the bottom surface of the rotary plate and is welded to an inner power supply line of the heater, and
one outer rolling ball body that is comprised of plurality of metal rolling balls located between the fixed outer metal ring and the upper outer metal ring, and
one inner rolling ball body that is comprised of plurality of metal rolling balls located between the fixed inner metal ring and the upper inner metal ring, and eight electric connecting wires, each of which, one end is welded to the heater and the other end is welded to upper metal ring, and four A/C power lines, two of which are welded to the inner fixing metal ring and the other two are welded to the outer fixing metal ring from the bottom side and connected to the main power source.

2. A rotary massager of claim 1, wherein the massager emits far infra-red ray and anion particle of 312 each/cm$^3$ at the same time while the massaging balls rotate.

* * * * *